United States Patent
Bathe et al.

[11] Patent Number: 5,977,112
[45] Date of Patent: Nov. 2, 1999

[54] PROCESS OF MAKING SUBSTITUTED BENZOFURANS

[75] Inventors: Andreas Bathe, Darmstadt; Bernd Helfert, Ober-Ramstadt; Henning Bottcher, Darmstadt; Kurt Schuster, Ober-Ramstadt, all of Germany

[73] Assignee: Merck Patent Gesellschaft mit beschrankter Haftung, Darmstadt, Germany

[21] Appl. No.: 08/960,459

[22] Filed: Oct. 29, 1997

Related U.S. Application Data

[62] Division of application No. 08/634,825, Apr. 19, 1996, Pat. No. 5,723,614.

[30] Foreign Application Priority Data

Apr. 20, 1995 [DE] Germany .......................... 195 14 567

[51] Int. Cl.⁶ ........................ A01N 43/58; C07D 403/00; C07D 413/00; C07D 405/00
[52] U.S. Cl. .......................... 514/254; 544/366; 544/368; 544/370; 544/376
[58] Field of Search .................... 544/376, 366, 544/370, 368; 514/254

[56] References Cited

U.S. PATENT DOCUMENTS 5,532,241 7/1996 Böttcher et al. ........................ 514/254

FOREIGN PATENT DOCUMENTS 712.844 6/1995 European Pat. Off. .
43 33 254 9/1993 Germany .
4333254 4/1995 Germany .

OTHER PUBLICATIONS

Millan et al., "A Naphtylpiperazine . . . Receptors," *Journal of Pharmacology & Exper. Therap.*, vol. 262, pp. 451–463 (1992).

Ramachandran et al., "The Synthesis of Euparin . . . ," *J. Org. Chem.*, vol. 28, No. 10, Oct. 1963, pp. 2744–2746.

Erlenmeyer et al., "Zur Kenntnis des . . . ," Helvetica Chica Acta., vol. 31, pp. 75–77 (1948).

Kahovcova et al., "Natural and Synthetic Materials With Insect . . . ," *Collection of Czech. Chem. Comm.*, vol. 38, No. 4, pp. 1165–1167 (1973).

*Primary Examiner*—Mukund J. Shah
*Assistant Examiner*—Tamthom N. Truong
*Attorney, Agent, or Firm*—Millen, White, Zelano & Branigan, P.C.

[57] ABSTRACT

Benzofurans of the formula I

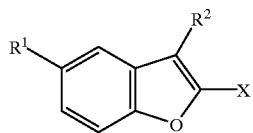

and their salts in which
$R^1$, $R^2$ and X have the meanings indicated in claim 1, are suitable as intermediates in the synthesis of medicaments and show effects on the central nervous system.

5 Claims, No Drawings

PROCESS OF MAKING SUBSTITUTED BENZOFURANS

This is a division of the application Ser. No. 08/634,825 filed Apr. 19, 1996 U.S. Pat. No. 5,723,614.

SUMMARY OF THE INVENTION

The invention relates to benzofurans of the formula

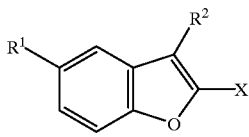

in which
$R^1$ is $NH_2$, 1-piperazinyl or 4-$R^3$-piperazinyl,
$R^2$ is H, Cl, Br, OH or OA,
$R^3$ is benzyl or an amino protective group which is known per se,
X is CN, COOH, COOA, COOPh, COOCH$_2$Ph, COOPy, CONR$^4$R$^5$ or CO-Het,
$R^4$ and $R^5$ are each independently H, A or benzyl,
A is $C_{1-4}$ alkyl,
Ph is phenyl,
Het is imidazol-1-yl, triazol-1-yl or tetrazol-1-yl and
Py is pyridyl,
and their salts.

Similar compounds are disclosed in DE 43 33 254, corresponding to allowed U.S. Pat. No. 5,532,241.

The invention provides novel compounds which can be used, in particular, as intermediates in the synthesis of medicaments, but can also be used directly for the production of medicaments.

In particular, they are active on the central nervous system especially in terms of 5-HT$_{1a}$-agonist and 5-HT-reuptake inhibition. The compounds are furthermore active as serotonin agonists and antagonists. They inhibit the binding of tritiated serotonin ligands to hippocampal receptors (Cossery et al., European J. Pharmacol., 140: 143–155 (1987)). They also modify the accumulation of DOPA in the corpus striatum and the accumulation of 5-HTP in the nuclei raphes (Seyfried et al., European J. Pharmacol., 160: 31–41 (1989)). They also have analgesic and hypotensive effects; thus, in catheterized, conscious, spontaneously hypertensive rats (strain: SHR/Okamoto/NIH-MO-CHB-Kisslegg; method: q.v. Weeks and Jones, Proc. Soc. Exptl. Biol. Med., 104: 646–648 (1960)), the directly measured blood pressure is lowered after oral administration of the compounds. They are also useful for prophylaxis and control of the sequelae of cerebral infarction (apoplexia cerebri) such as stroke and cerebral ischaemia.

It has been found that the compounds of the formula I and their salts are important intermediates for the production of medicaments and at the same time have pharmacological properties. Thus, they show, for example, effects on the central nervous system.

The invention relates to the benzofuran derivatives of the formula I and their salts.

Above and below, the radicals $R^1$, $R^2$, $R^3$, $R^4$, $R^5$, $R^6$, X, $X^1$, A, Ph, Bet and Py have the meanings indicated in the formulae I to VI, if not expressly stated otherwise.

In the above formulae, A has 1 to 4, preferably 1, 2 or 3, C atoms. A in preferably methyl or ethyl, furthermore propyl or isopropyl, and further also butyl, isobutyl, sec-butyl or tort-butyl.

The radical Ph is phenyl.
The radical Net in an imidazole, triazole or tetrazole which is attached through the 1-position.
The radical Py is preferably a pyridin-2-yl radical, and further also a pyridin-4-yl radical.
The radical X is CN, COON, COOA, COOPh, COOCH$_2$Ph, COOPy, CONR$^4$R$^5$ or CO-Het.
The radical $R^1$ is $NH_2$, 1-piperazinyl or a 1-piperazinyl radical substituted in the 4-position by $R^3$.
The radical $R^2$ is H, Cl, Br, OH or OA.
The radical $R^3$ is benzyl, but preferably an amino protective group known per se.

The expression "amino protective group" is generally known and relates to groups which are suitable for protecting (for blocking) an amino group from chemical reactions, but which are easily removable after the desired chemical reaction has been carried out in other positions of the molecule. Typical of such groups are, in particular, unsubstituted acyl, aryl, aralkoxymethyl or aralkyl groups. As the amino protective groups are removed after the desired reaction (or reaction sequence), their nature and size is otherwise uncritical; preferred groups, however, are those having 1–20, in particular 1–8 C atoms. The expression "acyl group" is to be interpreted in the widest sense in connection with the present process and the present compounds. It includes acyl groups derived from aliphatic, araliphatic, aromatic or heterocyclic carboxylic acids or sulfonic acids and also, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloroethoxycarbonyl, BOC (tert-butoxycarbonyl), 2-iodoethoxycarbonyl; aralkyloxycarbonyl such as CBZ (carbobenzoxycarbonyl, i.e., benzyloxycarbonyl, also called "Z"), 4-methoxybenzyloxycarbonyl, FMOC (9-fluorenylmethoxycarbonyl); arylsulfonyl such as Mtr (4-methoxy-2,3,6-trimethylphenylsulfonyl). Preferred amino protective groups are BOC and Mtr, and further CBZ or FMOC.

The compounds of the formula I can have one or more chiral centers and therefore occur in various stereoisomeric forms. The formula I includes all these forms.

The invention further relates to a process for the preparation of benzofurans of the formula I and of their salts, characterized in that a compound which corresponds to the formula I
in which $R^1$ is a nitro group,
is reduced in a customary manner, or
in that a compound which corresponds to the formula I
in which $R^1$ is an $NH_2$ group,
is reacted with a compound of the formula II $$R^6N(CH_2CH_2X^1)_2 \tag{II}$$

in which
$R^6$ is H or benzyl and
$X^1$ is Cl, Br, I, OH or a reactive functionally modified OH group, or
in that a compound which corresponds to the formula I in which $R^1$ is a 1-piperazinyl radical, is converted by introduction of an amino protective group known per se into another compound of the formula I in which $R^1$ is the 4-$R^3$-piperazinyl radical
in which $R^3$ has the meaning indicated, or in that a compound which corresponds to the formula I
in which X is a COOA group in which A has the meaning indicated,
is converted into another compound of the formula I in which X is $CONR^4R^5$ in which $R^4$ and $R^5$ have the meanings indicated, or
in that a compound which corresponds to the formula I in which X is a COOH group,
is converted into another compound of the formula I in which X is CO-Het in which Het has the meaning indicated, or
in that a compound which corresponds to the formula I in which $R^1$ is a 4-$R^3$-piperazinyl group in which $R^3$ has the meaning indicated,
is converted by removal of the protective group into a compound of the formula I in which $R^1$ is 1-piperazinyl and/or
in that a base of the formula I is converted into one of its salts by treatment with an acid.

One of ordinary skill in the art would be readily able to perform these reactions in analogy to those using similar reactants, for example, those reactions disclosed in Houben-Weyl, infra.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. In this case, use can also be made of variants which are known per se but not mentioned here in greater detail.

If desired, the starting substances can also be formed in situ such that they are not isolated from the reaction mixture, but immediately reacted further to give the compounds of the formula I.

In the compounds of the formula II, the radical $X^1$ is preferably Cl or Br; however, it can also be I, OH or a reactive functionally modified OH group such as alkylsulfonyloxy having 1–6 C atoms (preferably methylsulfonyloxy) or arylsulfonyloxy having 6–10 C atoms (preferably phenyl- or p-tolylsulfonyloxy, 1-or 2-naphthalenesulfonyloxy).

In the compounds of the formula II, the radical $R^6$ is H or benzyl. The compounds of the formula II are known in some cases; the unknown compounds can easily be prepared analogously to the known compounds.

The reaction of the compounds of the formula II with compounds of the formula I in which $R^1$ is $NH_2$ proceeds according to methods such as are known from the literature for the alkylation of amines. The components can be fused with one another without a solvent being present, if appropriate in a closed tube or in an autoclave.

However, it is also possible to react the compounds in the presence of an inert solvent.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; nitro compounds such as nitromethane or nitrobenzene; esters such as ethyl acetate, and optionally also mixtures of the solvents mentioned with one another or mixtures with water.

The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylamine, pyridine or quinoline or of an excess of the amine component can be favorable. Depending on the conditions used, the reaction time can be between a few minutes and 14 days, and the reaction temperature between 0 and 150°, normally between 20 and 130° C.

The conversion of a compound of the formula I in which $R^1$ is a nitro group into a compound of the formula I in which $R^1$ is an amino group is preferably carried out using hydrogen gas under transition metal catalysis (for example by hydrogenation on Raney nickel or Pd-carbon in an inert solvent such as methanol or ethanol).

The conversion of a compound of the formula I in which $R^1$ is a 1-piperazinyl radical into a compound of the formula I in which $R^1$ is the 4-$R^3$-piperazinyl radical is carried out according to known methods, such as are described in the literature (e.g. in the standard works such as Houben-Weyl, Methoden der organischen Chemie [Methods of Organic Chemistry], Georg-Thieme-Verlag, Stuttgart); e.g. for the alkylation or acylation of amines, namely under reaction conditions which are known and suitable for the reactions mentioned. In this case, use can also be made of variants which are known per se but not mentioned in greater detail here.

The conversion of a compound of the formula I in which X is a carboxyl group into a compound of the formula I in which X is COOA, COOPh, $COOCH_2Ph$, COOPy or CO-Net is carried out according to known methods, such as are described in the literature (e.g. in the standard works such as Houben-Weyl, Methoden der organischen Chemie [Methods of Organic Chemistry], Georg-Thieme-Verlag, Stuttgart) for esterifications or amidations of this type, namely under reaction conditions which are known and suitable for the reactions mentioned. In this case, use can also be made of variants which are known per se but not mentioned here in greater detail.

The conversion of compounds of the formula I in which X is COOA into compounds of the formula I in which X is COOH is carried out, for example, using NaOH or KOH in water, water-TEF or water-dioxane at temperatures between 0 and 100°.

The conversion of compounds of the formula I in which X is CN, COOH, COOA, COOPh, $COOCH_2Ph$, COOPY or CO-Het into compounds of the formula I in which X is $CONR^4R^5$ is carried out, for example, using $HCONR^4R^5$ in an inert solvent such as indicated above, if appropriate with addition of a base. The base used is, for example, a potassium or sodium alkoxide such as potassium or sodium methoxide, ethoxide or tert-butoxide.

The removal of a radical $R^3$ from a compound of the formula I is carried out—depending on the protective group used—for example with strong acids, expediently with TFA (trifluoroacetic acid) or perchloric acid, but also with other strong inorganic acids such as hydrochloric acid or sulfuric acid, strong organic carboxylic acids such as trichloroacetic acid or sulfonic acids, such as benzene- or p-toluenesulfonic acid. The presence of an additional inert solvent is possible, but not always necessary. Suitable inert solvents are preferably organic, for example carboxylic acids such as acetic acid, ethers such as tetrahydrofuran or dioxane, amides such as dimethylformamide, halogenated hydrocarbons such as dichloromethane, further also alcohols such as methanol, ethanol or isopropanol and also water. Mixtures of the abovementioned solvents are also suitable. TFA is preferably used in an excess without addition of a further solvent, perchloric acid in the form of a mixture of acetic acid and 70% perchloric acid in the ratio 9:1. The reaction temperatures are expediently between approximately 0 and approximately 50°; the reaction is preferably carried out between 15 and 30°.

The group BOC is preferably removed using TFA in dichloromethane or using approximately 3 to 5 N hydrochloric acid in dioxane at 15–30°.

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents here are those indicated above, in particular, for example, alcohols such as methanol or ethanol or amides such as DMF. The hydrogenolysis is generally carried out at temperatures between approximately 0 and 100° and pressures between approximately 1 and 200 bar, preferably at 20–30° and 1–10 bar.

A base of the formula I can be converted into the associated acid addition salt using an acid, for example by reaction of equivalent amounts of the base and of the acid in an inert solvent such as ethanol and subsequent evaporation. Suitable acids for this reaction are in particular those which give physiologically acceptable salts. Thus, inorganic acids can be used, e.g. sulfuric acid, nitric acid, hydrohalic acids such as hydrochloric acid or hydrobromic acid, phosphoric acids such as orthophosphoric acid, sulfamic acid, further organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, e.g. picrates, can be used for the isolation and/or purification of the compounds of the formula I.

On the other hand, compounds of the formula I can be converted using bases (e.g. sodium or potassium hydroxide or carbonate) into the corresponding metal, in particular alkali metal or alkaline earth metal salts, or into the corresponding ammonium salts.

The invention also relates to medicaments of the formula I and their physiologically acceptable salts.

The invention furthermore relates to the use of the compounds of the formula I as intermediates for the synthesis of medicaments. Corresponding medicaments are described, for example, in DE 4333254.

The invention accordingly relates in particular to the use of the compounds of the formula I according to claim 1 in the synthesis of 1-[4-(5-cyanoindol-3-yl)butyl]-4-(2-carbamoylbenzofuran-5-yl)piperazine and its salts, characterized in that 2-(2-formylphenoxy)acetic acid is nitrated, the 2-(2-formyl-4-nitrophenoxy)acetic acid thus obtained is cyclized, the 5-nitrobenzofuran-2-carboxylic acid thus obtained is esterified, the compound of the formula III thus obtained

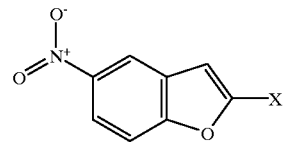

III in which X is COOA, COOPh or COOCH$_2$Ph,
is reduced,
the compound of the formula I thus obtained
in which R$^1$ is NH$_2$ and
X is COOA, COOPh or COOCH$_2$Ph
is converted into its acid addition salt and this is reacted with an acid addition salt of a compound of the formula II

HN(CH$_2$CH$_2$X$^1$)$_2$   II in which X$^1$ is Cl, Br, I, OH or a reactive functionally modified OH group,
to give a piperazine derivative of the formula IV

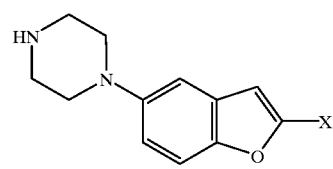

IV in which X is COOA, COOPh or COOCH$_2$Ph,
the compound of the formula IV thus obtained
is converted into its acid addition salt,
this is reacted with a compound which is suitable for the introduction of an amino protective group,
the compound of the formula V thus obtained

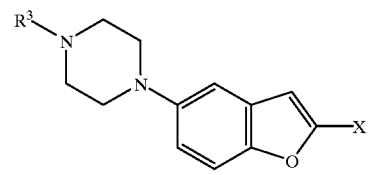

V in which R$^3$ is an amino protective group known per se and X has the meaning indicated,
is converted into a compound of the formula VI

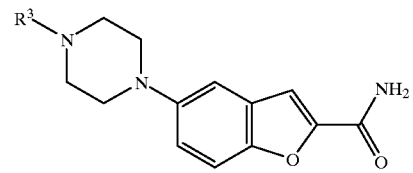

VI in which R$^3$ has the above meaning, the compound of the formula VI thus obtained is converted into 5-(1- piperazinyl)benzofuran-2-carboxamide or an acid addition salt by removal of the amino protective group and 5-(1-piperazinyl)benzofuran-2-carboxamide or a corresponding salt is reacted with 3-(4-chlorobutyl)-5-cyanoindole to give 1-[4-(5-cyanoindol-3-yl)butyl]-4-(2-carbamoylbenzofuran-5-yl)piperazine and optionally then converted into its acid addition salt.

3-(4-Chlorobutyl)-5-cyanoindole is disclosed in DE 4101686; 1-[4-(5-cyanoindol-3-yl)butyl]-4-(2-carbamoylbenzofuran-5-yl)piperazine is disclosed in DE 4333254.

The invention further relates to the use of the compounds of the formula I as intermediates for the synthesis of medicaments which show effects on the central nervous system.

The invention further relates to the use of the compounds of the formula I and/or of their physiologically acceptable salts for the production of pharmaceutical preparations, in particular by a non-chemical route. In this context, they can be brought into a suitable dose form together with at least one solid, liquid and/or semi-liquid excipient or auxiliary and if appropriate in combination with one or more further active compounds.

The invention further relates to pharmaceutical preparations comprising at least one compound of the formula I and/or one of its physiologically acceptable salts.

These preparations can be used as medicaments in human or veterinary medicine. Suitable excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc or petroleum jelly. Tablets, pills, coated tablets, capsules, powders, granules, syrups, juices or drops are used in particular for oral administration, suppositories for rectal administration, solutions, preferably oily or aqueous solutions, and further suspensions, emulsions or implants, for parenteral administration, and ointments, creams or powders for topical application. The novel compounds can also be lyophilized and the lyophilizates obtained used, for example, for the production of injection preparations. The preparations indicated can be sterilized and/or contain auxiliaries such as lubricants, preservatives, stabilizers and/or wetting agents, emulsifiers, salts for affecting the osmotic pressure, buffer substances, colorants, flavorings and/or several further active compounds, e.g., one or more vitamins.

The compounds of the formula I and their physiologically acceptable salts can be used in the control of illnesses.

The compounds of the formula I and their physiologically acceptable salts can be used for the therapeutic treatment of the human or animal body and for controlling diseases. They can be used for treating disorders of the central nervous system, such as tension, depressions and/or psychoses, and side-effects in the treatment of hypertension (e.g., with α-methyldopa). The compounds can also be used in endocrinology and gynecology, e.g., for the therapeutic treatment of acromegaly, hypogonadism, secondary amenorrhea, premenstrual syndrome and undesired puerperal lactation, and also for the prophylaxis and therapy of cerebral disorders (e.g., migraine), especially in the geriatrics in a manner similar to certain ergot alkaloids and for controlling the sequelae of cerebral infarction (apoplexia cerebri), such as stroke and cerebral ischemia.

In these treatments, the substances of the invention are normally administered analogously to known, commercially available preparations (e.g., bromocriptine, dihydroergocornine), preferably in dosages of about 0.2–500 mg, especially 0.5–20 mg per dosage unit. The daily dosage is preferably about 0.001–10 mg/kg of body weight. The low dosages (about 0.2–1 mg per dosage unit; about 0.001–0.005 mg/kg of body weight) are particularly suitable for use as anti-migraine preparations; dosages of about 10–50 mg per dosage unit are preferred for the other indications. However, the particular dose for each individual patient depends on a very wide variety of factors, for example, the activity of the particular compound used, age, body weight, general state of health, sex, diet, time and method of administration, rate of excretion, drug combination and severity of the particular disease to which the therapy is applied. Oral administration is preferred.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. DE 195 14 567.4, filed Apr. 20, 1995 are hereby incorporated by reference.

In the following examples, "customary working up" means: water is added, if necessary, the solution is adjusted, if necessary, to a pH between 2 and 10 depending on the constitution of the final product, and extracted with ethyl acetate or dichloromethane, the organic phase is separated off, dried over sodium sulfate, evaporated and purified by chromatography on silica gel and/or by crystallization. $R_f$ values on silica gel.

EXAMPLES

Example 1

A solution of 2.3 g of ethyl 5-nitrobenzofuran-2-carboxylate in 60 ml of methanol is hydrogenated in the presence of Raney nickel. The catalyst is filtered off and the solution is concentrated. After customary working up, ethyl 5-aminobenzofuran-2-carboxylate, $R_f$ 0.1 (dichloromethane/ethanol 9.5:0.5) is obtained; hydrochloride m.p. 246–248°.

Example 2

A solution of 2.05 g of ethyl 5-aminobenzofuran-2-carboxylate in 80 ml of dichloromethane is treated with 1.5 g of N,N-bis(2-chloroethyl)amine and stirred for 10 hours. The mixture is worked up in the customary manner and ethyl 5-(1-piperazinyl)benzofuran-2-carboxylate, $R_f$ 0.55 (isopropanol/water 95:5) is obtained.

Example 3

A solution of 1 g of ethyl 5-(1-piperazinyl)-benzofuran-2-carboxylate in 50 ml of THF is stirred with 1 g of di-tert-butyl dicarbonate for 3 hours. After customary working up, ethyl 5-(4-tert-butoxycarbonyl-1-piperazinyl) benzofuran-2-carboxylate, m.p. 116–118°, is obtained.

Example 4

A solution of 3 g of ethyl 5-(4-tert-butoxycarbonyl-1-piperazinyl)benzofuran-2-carboxylate in 100 ml of N-methylpyrrolidone is stirred for 5 hours with 1 g of formamide and 3 g of sodium alkoxide. After customary working up, 5-(4-tert-butoxycarbonyl-1-piperazinyl) benzofuran-2-carboxamide, m.p. 198–200°, is obtained.

Example 5

A solution of 1 g of ethyl 5-(1-piperazinyl)-benzofuran-2-carboxylate in 50 ml of dichloromethane is treated with 1 g of benzyl chloride and stirred for 2 hours. After customary working up, ethyl 5-(4-benzyl-1-piperazinyl)benzofuran-2-carboxylate, m.p. 219–222°, is obtained.

Example 6

1 g of 5-(4-tert-butoxycarbonyl-1-pipilrazinyl)-benzofuran-2-carboxamide is dissolved in 50 ml of methanolic HCl and stirred for 1 hour. After customary working up, 5-(1-piperazinyl)benzofuran-2-carboxamide, m.p. 252–255°, is obtained.

The following examples relate to pharmaceutical preparations:

Example A: Injection vials

A solution of 100 g of an active compound of the formula I and 5 g of disodium hydrogen phosphate is adjusted to pH 6.5 in 3 l of double-distilled water using 2 N hydrochloric acid, sterile filtered, filled into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into molds and allowed to cool. Each suppository contains 20 mg of active compound.

Example C: Solution

A solution is prepared from 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The solution is adjusted to pH 6.8, made up to 1 l and sterilized by irradiation. This solution can be used in the form of eye drops.

Example D: Ointment 500 mg of an active compound of the formula I is mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F: Coated tablets

Analogously to Example E, tablets are pressed which are then coated in a customary manner with a coating of sucrose, potato starch, talc, tragacanth and colorant.

Example G: Capsules 2 kg of active compound of the formula I are filled into hard gelatin capsules in a customary manner such that each capsule contains 20 mg of the active compound.

Example H: Ampoules

A solution of 1 kg of active compound of the formula I in 60 l of double-distilled water is sterile filtered, filled into ampoules, lyophilized under sterile conditions and aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process comprising converting a compound of formula IV

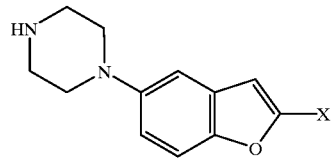

IV in which X is COOA, COOPh or $COOCH_2Ph$, to a compound of the formula V

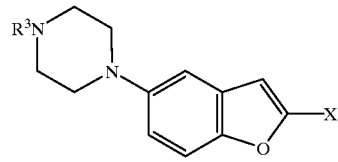

V in which $R^3$ is an amino protective group which is an acyl, aryl, aralkoxymethyl or aralkyl group, by inclusion of said amino-protecting group, and converting said compound of formula V into a compound of the formula VI

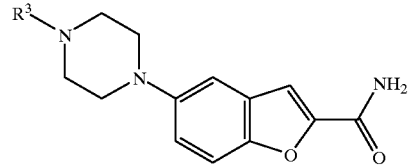

VI and deprotecting the amino group.

2. A process for the synthesis of 1-[4-(5-cyanoindol-3-yl)butyl]-4-(2-carbamoylbenzofuran-5-yl)piperazine or a salt thereof, comprising nitrating 2-(2-formylphenoxy)acetic acid, cyclizing 2-(2-formyl-4-nitrophenoxy)acetic acid thus obtained, esterifying 5-nitrobenzofuran-2-carboxylic acid thus obtained, reducing a compound of the formula III thus obtained

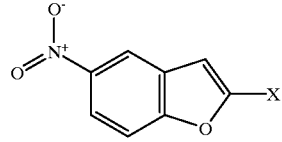

III in which X is COOA, COOPh or $COOCH_2Ph$, converting a compound of formula I' thus obtained

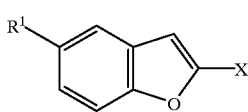

in which
R¹ is NH₂,
X is COOA, COOPh or COOCH₂Ph, and
A is C₁₋₄-alkyl,
into its acid addition salt and reacting the salt with an acid addition salt of a compound of the formula II

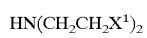

in which X¹ is Cl, Br, I, OH, or a reactive functionally modified OH group which is C₁₋₆-alkylsulfonyloxy or C₆₋₁₀-arylsulfonyloxy, to give a piperazine derivative of the formula IV

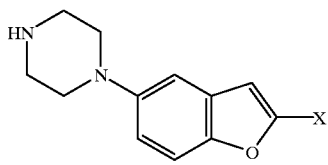

in which X is COOA, COOPh or COOCH₂Ph, converting a compound of the formula IV thus obtained into its acid addition salt, reacting the salt with a compound which is suitable for the introduction of an amino protective group which is an acyl, aryl, aralkoxymethyl or aralkyl group, converting a compound of the formula V thus obtained

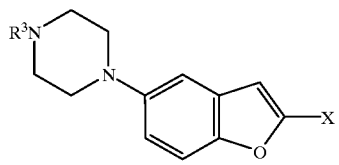

in which R³ is an amino protective group and X has the meaning indicated, into a compound of the formula VI

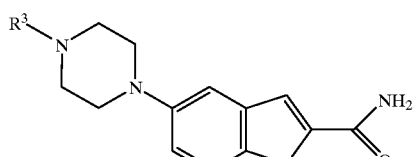

in which R³ has the above meaning,
converting a compound of the formula VI thus obtained into 5-(1-piperaziyl)-benzofuran-2-carboxyamide or an acid addition salt by removal of the amino protective group 5-(1-piperazinyl)benzofuran-2-carboxamide or an addition salt by removal of the amino protec-
tive group and reacting 5-(1-piperazinyl) benzofuran-2-carboxamide with 3-(4-chlorobutyl)-5-cyanoindole to give 1-[4-(5-cyanoindol-3-yl)butyl]4-(2-carbamoyl benzofuran-5-yl)-piperazine and optionally converting this compound into its acid addition salt.

3. A process according to claim 2, wherein the functionally modified OH group in X¹ is phenyl, p-tolylsulfonyloxy, or 1-or 2-naphthalenesulfonyloxy.

4. A process comprising converting a compound of formula VI

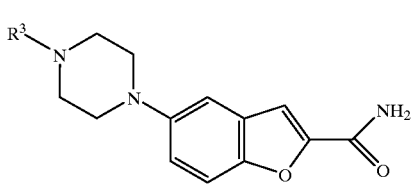

in which R³ is an amino protective group which is an acyl, aryl, aralkoxymethyl or aralkyl group, into 5-(1-piperaziyl)-benzofuran-2-carboxyamide or an acid addition salt by removal of the amino protective group 5-(1-piperazinyl) benzoftiran-2-carboxamide or an addition salt by removal of the amino protective group and reacting 5-(1-piperazinyl) benzofuran-2-carboxamide with 3-(4-chlorobutyl)-5-cyanoindole to give 1-[4-(5-cyanoindol-3-yl)butyl]4-(2-carbamoyl benzofuran-5-yl)-piperazine and optionally converting this compound into its acid addition salt.

5. A process for the synthesis of 1-[4-(5-cyanoindol-3-yl) butyl]-4-(2-carbamoylbenzofuran-5-yl)piperazine or a salt thereof, comprising nitrating 2-(2-formylphenoxy)acetic acid, cyclizing 2-(2-formyl-4-nitrophenoxy)acetic acid thus obtained, esterifying 5-nitrobenzofuran-2-carboxylic acid thus obtained, reducing a compound of the formula III thus obtained

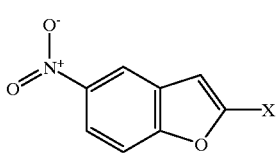

in which X is COOA, COOPh or COOCH₂Ph, converting a compound of formula I' thus obtained

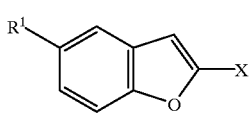

in which
R¹ is NH₂,
X is COOA, COOPh or COOCH₂Ph, and
A is C₁₋₄-alkyl,
into its acid addition salt and reacting the salt with an acid addition salt of a compound of the formula II

in which X¹ is Cl, Br, I or OH, to give a piperazine derivative of the formula IV

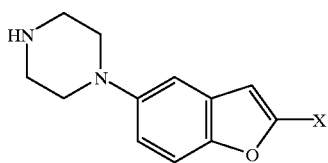

IV in which X is COOA, COOPh or COOCH$_2$Ph, converting a compound of the formula IV thus obtained into its acid addition salt, reacting the salt with a compound which is suitable for the introduction of an amino protective group which is an alkanoyl, aralkanoyl, aroyl, aryloxyalkanoyl, alkoxycarbonyl, aralkyloxycarbonyl, or arylsulfonyl group of 1–20 carbon atoms, converting a compound of the formula V thus obtained

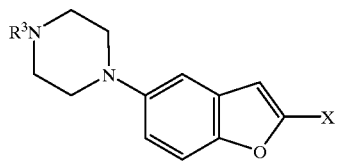

V in which R$^3$ is an amino protective group and X has the meaning indicated, into a compound of the formula VI

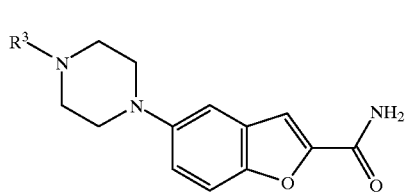

VI in which R$^3$ has the above meaning, converting a compound of the formula VI thus obtained into 5-(1-piperaziyl)-benzofuran-2-carboxyamide or an acid addition salt by removal of the amino protective group 5-(1-piperazinyl)benzofuran-2-carboxamide or an addition salt by removal of the amino protective group and reacting 5-(1-piperazinyl) benzofuran-2-carboxamide with 3-(4-chlorobutyl)-5-cyanoindole to give 1-[4-(5-cyanoindol-3-yl)butyl]4-(2-carbamoyl benzofuran-5-yl)-piperazine and optionally converting this compound into its acid addition salt.

* * * * *